(12) United States Patent
Kujawski

(10) Patent No.: US 6,306,164 B1
(45) Date of Patent: Oct. 23, 2001

(54) SHORT BODY ENDOPROSTHESIS

(75) Inventor: Dennis Kujawski, Brookline, NH (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 08/925,809

(22) Filed: Sep. 5, 1997

(51) Int. Cl.[7] ........................................ A61F 2/00
(52) U.S. Cl. ................. 623/1.35; 623/1.36; 623/1.16
(58) Field of Search ................... 623/1, 11, 12, 623/1.13, 1.16, 1.23, 1.27, 1.35, 1.36

(56) References Cited

U.S. PATENT DOCUMENTS

| | | | |
|---|---|---|---|
| 5,562,724 | * | 10/1996 | Vorwerk et al. ........................ 623/1 |
| 5,591,228 | * | 1/1997 | Edoga ................................ 623/1.23 |
| 5,609,627 | * | 3/1997 | Goicoechea et al. ................. 623/1 |
| 5,632,772 | * | 5/1997 | Alcime et al. ........................ 623/1 |
| 5,639,278 | * | 6/1997 | Dereume et al. ..................... 623/1 |
| 5,824,040 | * | 10/1998 | Cox et al. ......................... 623/1.35 |
| 5,843,160 | * | 12/1998 | Rhodes ............................. 623/1.35 |
| 5,944,750 | * | 8/1999 | Tanner et al. ....................... 623/1.23 |

\* cited by examiner

Primary Examiner—Michael J. Milano
(74) Attorney, Agent, or Firm—Foley, Hoag & Eliot LLP

(57) ABSTRACT

The invention comprises, inter-alia, endoprosthetic implants for treating vascular defects, including abdominal aortic aneurysms. Implants according to the invention have a short main body that can be positioned within a patient's aorta at a position above the renal end of an aortic aneurysm. The short main body includes a proximal, or renal, face that redirects the flow of blood into the openings of channels that can carry blood past the aneurysm. In this way, the flow of blood through the aorta is diverted into the two passageways and through the main body of the implant. Fluid exiting the implant can be carried by leg extensions and delivered to a healthy part of the patient's aorta or the iliac arteries. Accordingly, the implant provides a system for allowing blood traveling through the aorta to be carried by a vascular graft that spans an aortic aneurysm, thereby relieving fluid pressure on the thin wall of aortic aneurysm, and reducing the risk of death caused by a ruptured aneurysm.

15 Claims, 10 Drawing Sheets

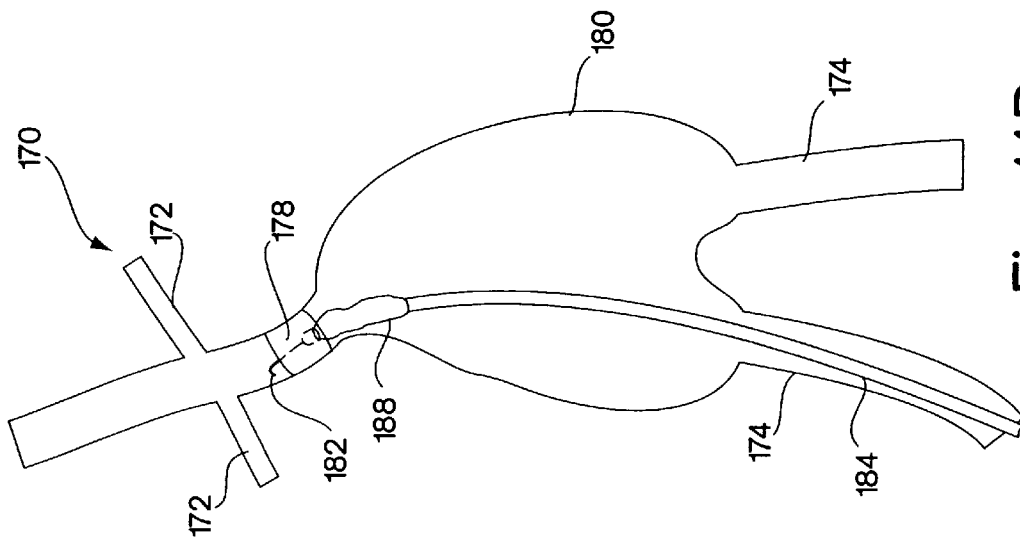
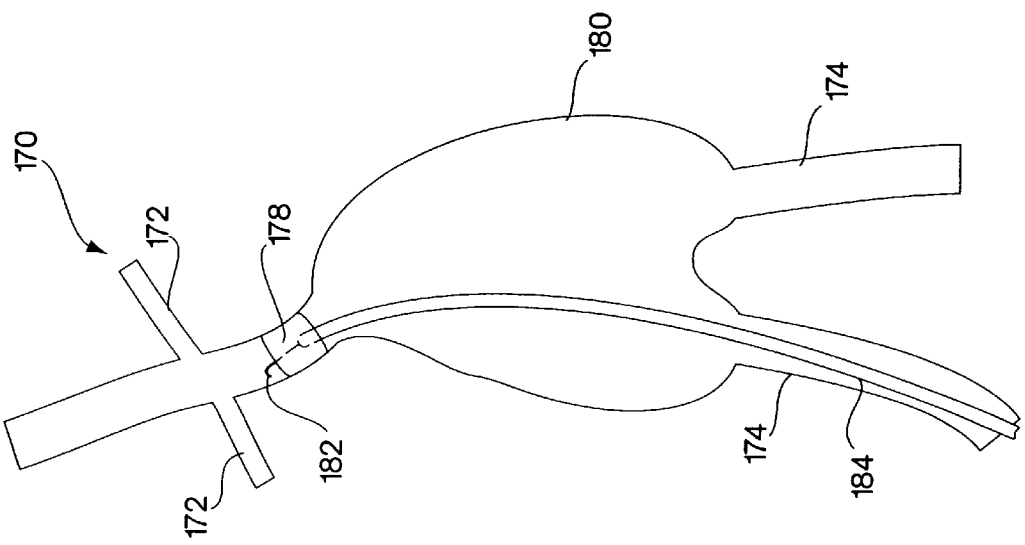

SHORT BODY ENDOPROSTHESIS

FIELD OF THE INVENTION

The invention relates to systems and methods for treating vascular disorders, including conditions affecting bifurcated blood vessels.

BACKGROUND OF THE INVENTION

Diseases of the vascular system afflict a substantial portion of the adult population. Many of these diseases are life-threatening conditions that demand substantial surgical intervention. For example, an aortic aneurysm is a particularly troubling medical condition in which a localized abnormal dilation of the aorta occurs. At the site of the dilation the aorta wall becomes thin and weak, giving rise to a substantial danger of rupture and death by internal hemorrhaging. Although there are traditional surgical procedures that can be effective in treating conditions like an aortic aneurysm, the surgery itself can be taxing and dangerous for the patient. In particular, for an aortic aneurysm the surgical procedure requires that the patient's abdominal cavity be opened to reach and expose the aortic aneurysm. The patient is maintained on an independent life support system while the aneurysm is incised lengthwise to enable insertion of a vascular graft into the aorta that spans the weakened section of the aorta to carry blood between the remaining healthy portions. This is a highly invasive and dangerous surgical procedure that requires that the surgeon balance the patient's risk of harm from the aneurysm against the patient's risk of harm from the treatment. Today, approximately 50,000 abdominal aortic aneurysms are surgically repaired annually in the United States. However, more aneurysms are left untreated than treated as much of the afflicted population is ill or frail and therefore unlikely to survive the surgery.

To reduce the mortality and morbidity resulting from these highly invasive surgical procedures, and to provide surgical treatments suitable for treating a broad range of patients, catheter delivery systems have been developed that allow a vascular graft to be inserted within the patient's vascular system through a small incision made within a peripheral artery of the patient. The catheter is fed through the patient's artery and to the sight of the diseased or compromised vascular tissue. A graft is then passed through an interior channel of the catheter and disposed within the patient's vascular system to support, or supplant, the diseased tissue. Typically, the graft is an implantable endovascular stent-graft that is tubular in shape and that is adapted to act as a prosthetic artery for removing pressure from the weakened aortic wall. Upon delivery of the graft, the catheter is removed from the patient's vascular system and the small incision is closed. Accordingly, these systems for the transluminal delivery of endovascular grafts bypass the need for highly invasive surgical procedures, such as abdominal surgery, by allowing a doctor to use the patient's natural body lumens as pathways for reaching the diseased tissue within the vascular system.

Today, there are a variety of existing transluminal delivery systems and endovascular grafts for treating vascular conditions such as aortic aneurysms. One class of these systems is directed to the treatment of abdominal aortic aneurysms that are proximate or extend into the iliac arteries. These systems provide for the delivery of a bifurcated endovascular graft that includes a main body that attaches within the descending aorta and a bifurcated portion that includes two legs, each of which is an endovascular graft, and each of which couples to the main body and carries blood to a respective one of the iliac arteries.

In some systems, the bifurcated graft is a single unit that includes the main body and two legs. In these systems, the treating surgeon uses one or more catheters to deliver the graft to the site of the aneurysm and in a cumbersome process the surgeon releases the graft from the catheters and arranges the main body of the graft within the aorta and the legs within the two iliac arteries. As an alternative to this cumbersome process, bio-medical engineers have developed modular endovascular grafts that include a main body and one or more separate leg grafts. These modular designs eliminate the need for the surgeon to arrange the graft within the patient's aneurysm. Instead, the surgeon forms the graft by transluminally delivering each piece of the graft in such a way that during each subsequent delivery, a new piece is aligned and positioned to join with the previously delivered pieces and to form the complete endovascular graft.

Although these modular endovascular grafts can provide an effective treatment, their application is generally limited to aneurysms that occur within aortas that are substantially straight and only moderately transverse to the patient's iliac arteries. In part, this is because the process of assembling the modular graft requires that the pieces be readily and precisely aligned and positioned during delivery. However, an unfortunate side effect of some vascular diseases, including aneurysms, is that tissue growth can occur at the site of the diseased vessel. This can cause the diseased aorta to lengthen. Due to its confinement within the abdominal cavity, the lengthening aorta often twists and loops into a torturous configuration. For several reasons, patients with twisted aortas are often poor candidates for receiving modular endovascular grafts through transluminal delivery. For example, it may be difficult for the surgeon to achieve the necessary alignment for delivering the different pieces of the modular endovascular graft. Further, the twisted aorta often has only a short renal neck of healthy tissue to which the main body of the graft may attach. Therefore, the surgeon may only be able to place a limited portion of the main graft body into the short renal neck, leaving a large section of the graft to extend into the aneurysm at an angle that can be significantly transverse to the iliac arteries through which the delivery catheter travels. In these cases, it may not be possible for the surgeon to snake the guidewire that is used to deliver the other components of the modular graft through the iliac artery and into the portion of the modular endovascular graft that extends into the aneurysm. Consequently, for many of these patients, the only viable solution is to have abdominal surgery and to incise the compromised aortic tissue and supplant this tissue with a vascular graft.

Accordingly, it would be desirable to provide endoprosthetic implants, including modular endovascular grafts, that are suited for disposition within body lumens, including short or torturous body lumens, to thereby provide a minimally invasive surgical procedure suitable for application in a broad class of vessels.

SUMMARY OF THE INVENTION

Accordingly, it is an object of the invention to provide an improved endoprosthetic implant adapted to be placed within a torturous body lumen.

It is a further object of the invention to provide an endoprosthetic implant that is facile to position and reposition within a body lumen.

It is yet another object of the invention to provide a modular endoprosthetic implant that is facile to assemble within a patient's body lumen.

Other objects of the invention will in part, be set forth below and, in part, be obvious to one of ordinary skill in the art given the following description The invention includes, inter alia, systems and methods for treating vascular disorders such as aneurysms. The systems of the invention include modular endovascular grafts that fit within a short lumen, or a short portion of a lumen, and that can be delivered transluminally and assembled in situ to provide an endovascular graft that supports or supplants a portion of the patient's vascular system. In one embodiment, the modular endovascular graft includes two types of components, a trunk that can fit within a body lumen, such as the aorta, and a leg extension adapted for carrying blood. The trunk is adapted to engage against the interior tissue wall of the lumen. The trunk can have a proximal face with an opening to a channel that extends through the trunk to provide thereby a fluid path for, in one application, redirecting circulating blood to pass through the channel. The proximal face can be dimensionally adapted so that the outer perimeter of the face abuts the interior tissue wall of the lumen in which the trunk is placed. Thus, a seal can be formed that prevents, or reduces, blood from flowing or leaking into the aneurysm by passing between the periphery of the trunk and the tissue wall. Accordingly, the trunk forms a collar that fits within and seals against the interior wall of the lumen. The channel of the trunk is adapted to receive or otherwise engage a leg extension that can be a vascular graft for carrying blood from the channel of the trunk to an alternate location within the patient's vascular system. To this end, the leg extension and channel can form a substantially fluid-tight seal to create a continuous fluid path from the proximal face of the trunk to the distal end of the leg extension. This continuous fluid path allows the endovascular graft to carry blood past a diseased portion of the vessel and to an alternate portion of the patient's vascular system. By carrying the blood, the endovascular graft removes the arterial blood pressure that is acting on the weakened wall of the aneurysm.

More particularly, in one aspect, the invention can be understood as an endoprosthetic implant that includes a trunk having a proximal face that has an opening to a channel that extends through the trunk. An anchor is coupled to the periphery of the face and is adapted for engaging the face against an interior tissue wall of a body lumen. In this embodiment the proximal face can include a substantially flat surface formed of a fluid resistant, biocompatible material suitable for disposition within a flow of fluid that occurs within the body lumen. The proximal face can be dimensioned so that in an expanded condition the outer periphery of the face seals against the tissue wall of the lumen to redirect the fluid flow through the channel. In one particular embodiment, the endoprosthetic implant includes a short trunk that is dimensionally adapted for disposition within a body lumen at a location above the site of an aneurysm. For example, the short trunk can be dimensionally adapted to sit within the aorta at a position that is generally below the renal arteries and above the renal most section of the aneurysm. Optionally, the trunk could descend for a short distance into the aneurysm.

The terms proximal and distal as used herein will be understood to describe opposite ends of a device, channel or element, and generally will be employed so that proximal is understood as "towards the heart" and distal is understood as "away from the heart" or to mean upstream and downstream of fluid flow respectively.

The trunk can include an anchor that is disposed about the periphery of the trunk and that is centrally located with respect to the longitudinal axis of the trunk. In an alternative embodiment, the anchor can be disposed about the periphery of the trunk and adjacent the proximal face of the trunk. This can facilitate repositioning and recapture of the endoprosthetic implant. The anchor can include a tubular wire frame that supports the graft. The term tubular as employed herein will be understood to include any shape defined by a sidewall that includes at least two openings with a hollow space extending therebetween, and wherein the sidewall can be generally cylindrical, rectangular, triangular or any other shape.

An endoprosthetic implant according to the invention can further be understood to include tubular leg extensions each of which has an interior channel and an upper end being radially contractile for insertion into the channel of the trunk. The leg extensions can be dimensionally adapted for longitudinally spanning an aneurysm, to provide continuous lumens that extend across the aneurysm. The continuous lumens allows the implant to carry blood across the aneurysm to reduce pressure on the weakened tissue wall and reduce the risk of rupturing.

In a further embodiment, the endoprosthetic implant can include hooks that are coupled to the trunk for securing the trunk to the walls of the body lumen. The hooks can be small, metal projections that are directed outwardly from the trunk to grip the tissue wall. However, the term hook will be understood to encompass multi-prong claws, pawls, detents or any suitable device for enhancing the security of the engagement of the trunk to the vessel wall or for preventing or reducing movement of the implant within the patient, and particularly for reducing downstream movement of the implant caused by the force of circulating blood.

Other embodiments of the invention can include endoprosthetic implants that include a trunk that comprises a solid plug of biocompatible material. The solid plug can have two interior channels, or passageways, that extend therethrough for defining the first and second channels. The plug can be comprised of a biodurable and biocompatible material such as PTFE or other suitable material.

Alternatively, the endoprosthetic implant can comprise a bifurcated stent and vascular graft that wraps around the body of the bifurcated stent or, optionally, fits inside the body of the bifurcated stent. The bifurcated stent can be radially compressible and radially expandable to allow for transluminal delivery. Optionally, the stent can be selfpanding or can be expanded by action of an inflating balloon. The graft can be a biocompatible material, such as Dacron™, or PTFE.

In another aspect, the invention can be understood as methods for providing a bifurcated implant within a body lumen. The methods of the invention can include the steps of providing a trunk having a proximal face and having a first and second channel extending longitudinally through the trunk, and a second step of disposing the trunk within the body lumen and orienting the proximal face to obstruct substantially a flow of fluid moving through the body lumen, whereby fluid flow is redirected through said first and second channels.

Other aspects and embodiments of the invention will be apparent from the following description of certain illustrative embodiments.

BRIEF DESCRIPTION OF THE FIGURES

The following figures depict certain illustrative embodiments of the invention in which like reference numerals refer to like elements. These depicted embodiments are to be understood as illustrative of the invention and not as limiting in any way.

FIGS. 14a–14d depict one process for implanting an endovascular graft according to the invention.

DETAILED DESCRIPTION OF THE ILLUSTRATED EMBODIMENTS

Figure 1:
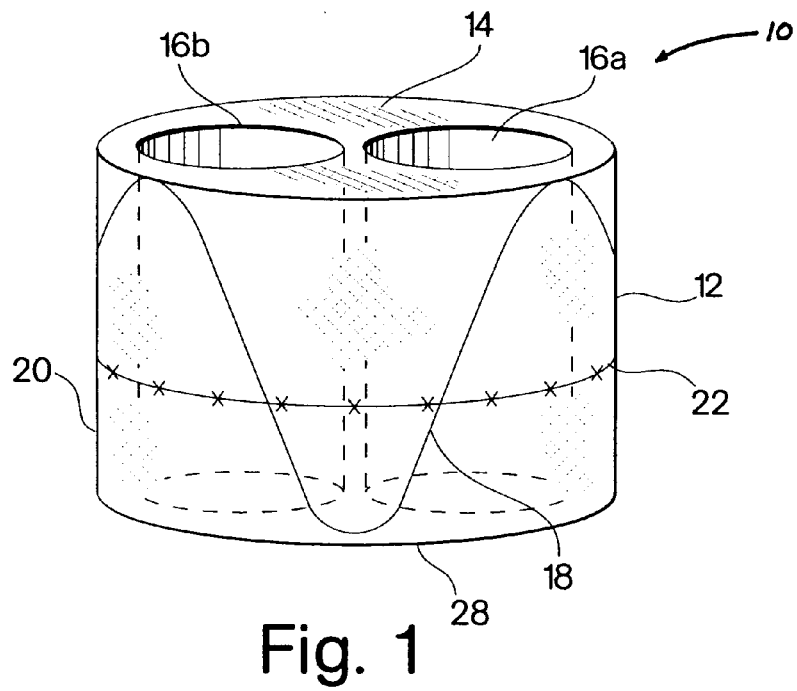
FIG. 1 depicts one trunk of an implant according to the invention.

To provide an overall understanding of the invention, the methods, systems and devices of the invention will be discussed with reference to the application of treating an aortic aneurysm. However, it will be understood by persons of ordinary skill in the art that the general methods, systems and devices described herein are equally applicable to all cases in which implants are provided for carrying fluids within the body. These applications can include vascular grafts for treating other aneurysms, lesions, grafts for carrying urine, grafts for carrying bile, grafts for creating subcutaneous injection ports for receiving fluids such as therapeutic agents and saline solution, or any other application requiring an implant to be located in a lumen of a patient. Other clinical uses of the invention can be made without departing from the scope of the invention.

The invention comprises, inter-alia, endoprosthetic implants, a subset of which can include a class of endovascular grafts for treating vascular defects such as abdominal aortic aneurysms. Implants according to the invention include a trunk that can have an interior channel that extends through the trunk. The trunk further includes a proximal face that can redirect a flow of fluid, such as circulating blood, into the channel. By employing a proximal face to redirect the flow of fluid, the trunk of the endoprosthetic implants has a shortened forward section and a reduced longitudinal dimension as compared to the trunks of prior art implants, such as the implant shown in PCT patent application PCT/DK94/00468 which employs a forward funnel-like portion for redirecting circulating blood. This allows the trunk of the endoprosthetic implant to be positioned within a short section of a body lumen and provides thereby an endoprosthetic implant that can be located within a body lumen that has been misshapen by disease, injury or birth defect and that has only a short section of healthy or properly formed tissue for receiving an endoprosthetic implant. In one embodiment, the endoprosthetic implant is an endovascular graft in which the trunk couples to a tubular vascular graft to reinforce or supplant a diseased or injured portion of the vascular system. In this embodiment, the channel extending through the trunk can couple with the vascular graft to form a continuous lumen for carrying blood. The graft can be a tubular conduit that is sufficiently long to span the diseased portion of the vasculature, to thereby carry blood to a healthy section of the lumen, or to an alternate lumen. This reduces or eliminates the pressure acting on the diseased lumen.

For illustrative purposes, the invention will now be described with reference to one illustrative embodiment that comprises a bifurcated endovascular graft for treating a bifurcated blood vessel, such as the abdominal aorta bifurcation to the common iliac arteries. In this embodiment, the trunk includes a pair of channels, or passageways, that extend through the trunk. The flow of blood through the vessel is diverted into the two channels and through the trunk of the implant. Blood exiting the channels can be carried by a leg extension and delivered to a healthy portion of the vessel, or to an alternate vessel, such as the common iliac arteries. Accordingly, the implant provides a system for allowing blood traveling through the aorta to be carried by a vascular graft that spans an aortic aneurysm, thereby relieving fluid pressure on the weakened wall of the aortic aneurysm, and reducing the risk of hemorrhaging and death caused by a ruptured aneurysm.

FIG. 1 depicts one embodiment of the trunk component that is one portion of an implant 10 according to the invention. In this embodiment, the implant 10 provides for a bifurcated flow of blood through a patient's vascular system. However, it will be apparent to one of ordinary skill in the art that implants of the invention can carry blood, urine or other fluid material.

In particular FIG. 1 depicts a trunk 12 having a renal face 14, channels 16a and 16b, an anchor 18, a graft 20 and a sewn 22. The depicted trunk 12 is a biocompatible, biodurable and implantable component suitable for disposition within a body lumen such as the aorta, and dimensioned such that the outer portion of the proximal face 14 seals against the interior tissue wall of the aorta and redirects the flow of blood through the channels 16a and 16b. In one embodiment, the trunk 12 extends approximately between 1.0 and 3.0 cm from the proximal face 14 to the distal face 28. As depicted in phantom in FIG. 1, the channels 16a and 16b extend from the proximal face 14 of the trunk 12 to the distal face 28, thereby providing two flow paths that extend through the trunk 12. Accordingly a flow of fluid, such as blood being carried by the aorta, is redirected by the renal face 14 into the channels 16a and 16b, such that a bifurcated flow of blood is created.

FIG. 1 provides a side-view perspective of the proximal face 14. The proximal face 14 can be substantially flat, having a slight concavity in which the central portion of the proximal face 14 is displaced approximately 1–5 mm. below the rim defined by the proximal end of the anchor 18. The material of the graft 20 can slightly bunch, ripple or fold depending on how fully the trunk expands within the patient's aorta, giving the proximal face 14 an uneven surface. Alternatively, the proximal face 14 can be intentionally given a slight taper or leading edge. This is understood to reduce the turbulence caused when the patient's blood passes through the implant.

Figure 2:
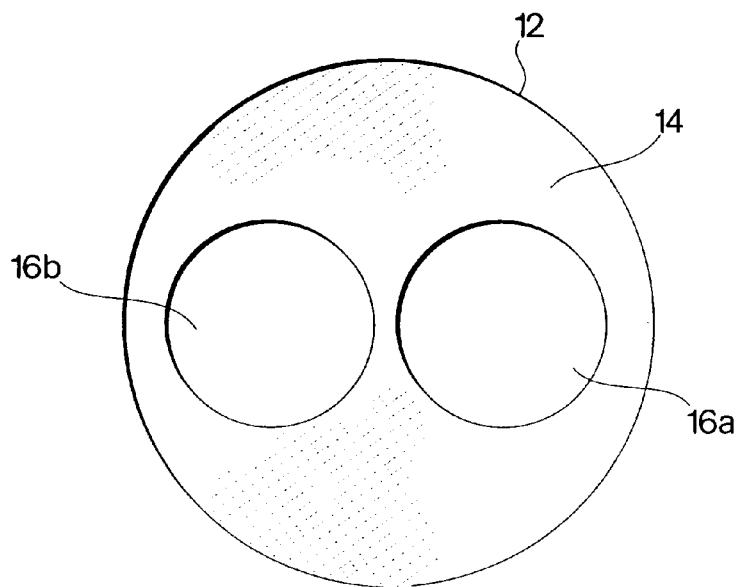
FIG. 2 provides an overhead perspective of the renal face of the trunk depicted in FIG. 1.

FIG. 2 provides an overhead perspective of the implant 10 and depicts the proximal face 14 of the trunk 12 to illustrate the open ends of the channels 16a and 16b. The proximal face 14 depicted in FIG. 2 has a diameter selected to fill the interior portion of the body lumen, and each of the channels 16a and 16b have diameters selected to allow sufficient fluid flow to other portions of the patient's vasculature. As discussed above, the endoprosthetic implant can be a bifurcated endovascular graft disposed in a patient's aorta to treat an abdominal aneurysm. For this embodiment, the proximal face 14 can be dimensioned to fill approximately the interior of the aorta, and can have a diameter of approximately 12 mm to 30 mm. Each of the channels 16a and 16b can be dimensioned to carry blood to the iliac arteries and can each have diameters of approximately 6 mm to 15 mm. The dimensions for the proximal face 14, the channels 16a and 16b, and the other components of the implant 10 can vary depending on the medical condition being treated and the size and location of the body lumen in which the implant is being disposed. Such dimensions will be apparent to one of ordinary skill in the art and can be ascertained by any of the known techniques, including by fluoroscopy.

With reference again to FIG. 1, it is shown that trunk 12 includes an anchor 18 that extends from the circumference of the proximal face 14 of the implant 10 to the circumference of the distal face 28. In the depicted embodiment, the graft 20 wraps around the anchor 18 and covers both sides of the anchor 18 with the material of the graft 20. For the depicted anchor 18, the ends of the graft are folded over the anchor 18 and a stitch 22 joins the ends of the graft to seal the anchor 18 within the graft 20. Consequently, no portion of the anchor 18 is directly exposed to the tissue of the aorta.

The anchor 18 includes a collapsible, flexible and self expanding wire frame which may be formed from any suitable wire such as of MP35N ™ alloys sold by SPS Technologies Inc., nitinol, or a stainless steel alloy. Optionally, the anchor 18 can also include hooks, detents or other means for securing the trunk to the tissue wall. The wire frame of the anchor 18 acts as a supporting frame for the graft 20 and, when in an expanded condition, serves to maintain the graft 20 in its open configuration. The wire frame defines a rim at its proximal end that can support the graft 20 and define the periphery of proximal ace 14. As part of the wire frame, the rim is collapsible and expandable. In the expanded condition, the rim of the wire frame pulls the material of the graft 20 tight enough to form the proximal face. In its collapsed condition, the anchor 18 is sufficiently radially reduced to fit within an transluminal delivery device and can have a collapsed radius of about 1 to 4 mm. The collapsed anchor 18 can generate an outwardly directed expansion force sufficient to engage the trunk 12 against the interior wall of the patient's aorta and to seal the periphery of the trunk 12 against the tissue of the aorta and prevent blood from passing between the implant and the tissue wall and leaking into the area of the aneurysm. Optionally, the anchor can fit against the tissue wall with sufficient force to maintain the implant 10 at a selected position within the aorta, being able to resist downward movement of the implant 10 caused by the downward pressure of the circulating blood. In this way, the anchor 18 can act as a compression fit that fixedly engages the implant within the patient and acts to reduce, or eliminate, downward movement of the implant caused by the pressure of the circulating blood. As the anchor 18 is radially expandable, the anchor 18 can continue to expand and fill the aorta, if the aorta distends at the location of the implant. Accordingly, the implant 10 can accommodate some distension of the aorta caused by the insertion of the implant. However, the depicted anchor 18 has generally a maximum achievable diameter, which prevents the anchor 18 from continually pressing against, and possibly distending the tissue wall of the aorta. Optionally, the anchor 18 can include detents, either at the distal or proximal ends, that extend outside of the graft and that grip the tissue wall of the aorta and thereby add additional support for resisting downward movement of the implant.

In the depicted embodiment, the anchor 18 includes a wire frame that is formed from a single wire that is shaped like a sine wave and that has its ends connected together to form a hoop for supporting the graft 20. FIG. 1 illustrates the wire frame of the anchor 18 in its expanded condition. In this expanded condition, the wire frame holds the graft 20 in an open configuration that holds the channels 16a and 16b open to receive blood traveling through the aorta. Similarly, the wire frame of the anchor 18 holds the openings of the channels 16a and 16b of the distal face 28 (not shown) open. This provides a stent-like function that allows leg extensions to be inserted within the distal ends of the channel 16a and 16b. It will be seen that the combined functions of the wire frame configuration of the anchor 18 depicted in FIG. 1 which acts both as support for the distal portion of the graft 20 and as a stent for maintaining the channels 16a and 16b open to receive iliac leg extensions, reduces the length of the distal portion of the trunk 12 by eliminating the need to have a distal stent or other device for receiving the iliac leg extensions.

Although the depicted anchor 18 has a frame formed from a single wire, it will be obvious to one of ordinary skill in the art, that other frame structures and geometries can be practiced with the invention without departing from the scope thereof For example, the wire frame of the anchor 18 can be formed of multiple elements, each of which forms one section of the wire frame. One such wire frame is depicted in FIG. 5b. Each of the sections depicted in FIG. 5b are identical and each is joined at its ends to two other sections. The sections can be joined by any suitable technique including welding. Optionally, the material employed can have a radio-opaque characteristic. Alternatively, the wire frame can be a Palmaz-type stent of stainless steel or of nitinol that expands in response to the patient's body temperature, or can be made from a braided wire stent. In a further embodiment, the wire frame could be a circular hoop that supports the graft material, so that the graft stretches over the rim of the hoop like a drumhead, thereby forming the proximal face. The channels could extend from the proximal face to provide a seating area for iliac leg extensions.

The graft 20 is formed of a bio-compatible and bio-durable material such as woven or knitted polyester, PTFE or any other suitable material. In one embodiment, the graft is formed from a fabric of tightly woven polyethylene terephthalate ("PET") fibers. The graft material is generally chosen by selecting materials having satisfactory long term use within the human body, and having the ability to withstand the stress applied by the blood pressure occurring in large vessels, such as the aorta. For an endovascular graft, the material of the graft 20 is preferably a hemo-compatible material and can be a porous material, such as woven polyester, that becomes fluid resistant as blood circulates through the implant 10 and forms a protein and fibrin layer on the graft 20. However, grafts employed for carrying urine, bile or other fluids may comprise materials that are selected for other characteristics that are more suited to these alternate applications.

Figure 3:
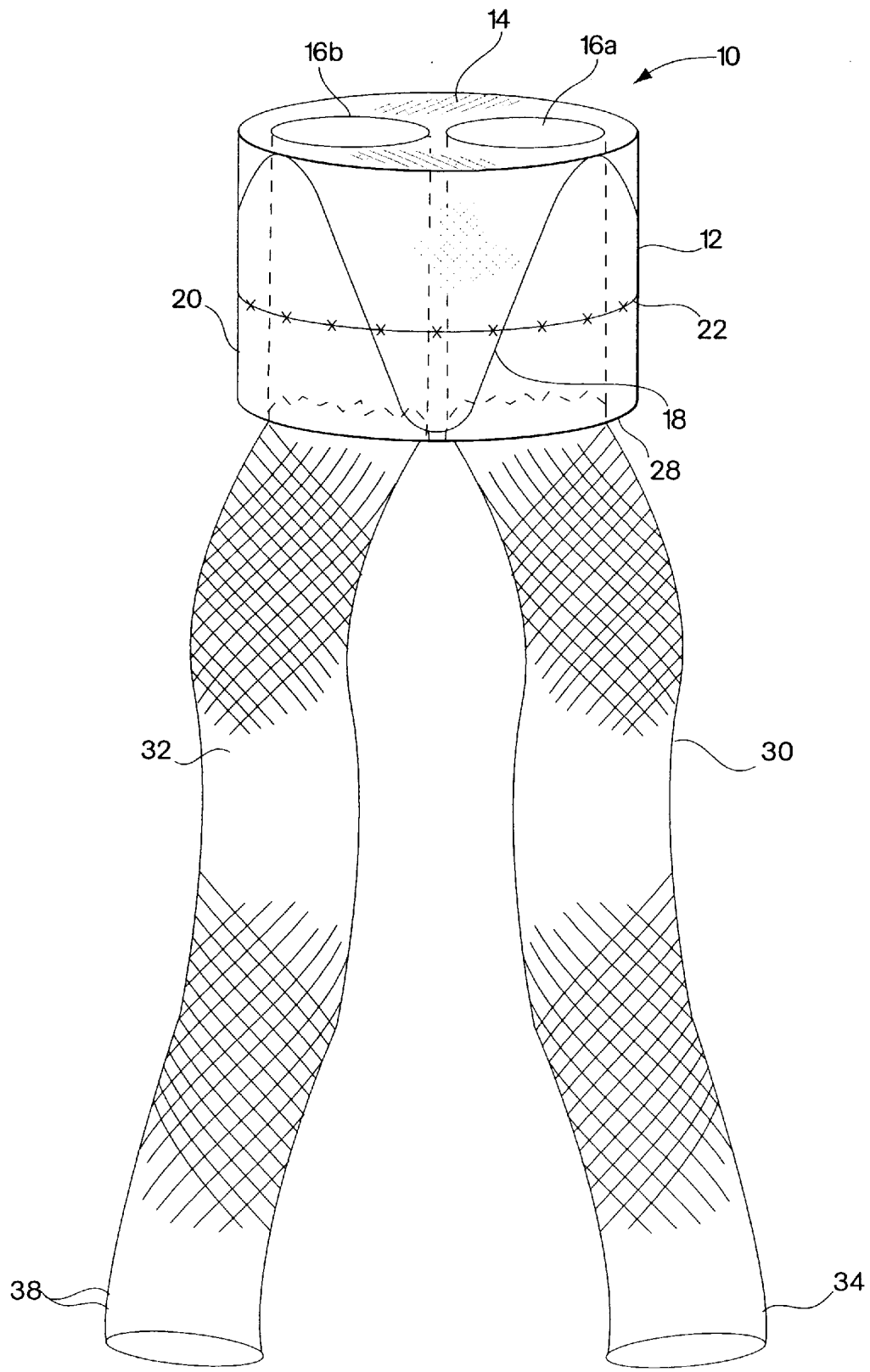
FIG. 3 depicts the trunk of FIG. 1 having two tubular leg extensions.

FIG. 3 depicts an implant 10 with two tubular iliac leg extensions, 30 and 32, extending from the distal face 28 of the trunk 12. Each of the tubular legs 30 and 32 couples in fluid communication to one of the channels 16a or 16b extending through the trunk 12 of the implant 10. In this way, the tubular legs 30 and 32, and the channels 16a and 16b form conduits for carrying blood through the vascular system of a patient. Accordingly, the trunk 12 of the implant 10 forms a narrow collar that engages a short portion of the patient's body lumen, and couples to one or more tubular leg extensions that carry blood from the collar to another portion of the patient's vascular system.

Each of the leg extensions, 30 and 32, can be a stent-graft of the type capable of being employed as a synthetic blood vessel and the length of the tubular leg extensions 30 and 32 may be selected to suit the anatomy of the particular patient and the particular application. The graft material of the legs 30 and 32 can be any suitable material, including polyester resins such as those sold by the Dupont Corporation and marketed under the name Dacron™, or any of the fabrics from which the graft 20 is formed. However, it will be understood by one of ordinary skill in the art that any of a variety of available graft materials may be employed with the leg extensions and can be selected to exploit certain characteristics of a particular material which are suited for the particular requirements of a patient or a treatment.

The stents of the legs 30 and 32 can support the graft, and the graft can be stitched, glued or otherwise attached to the body of the stent. In one embodiment, the stent is a Palmaz-type stent formed from a laser etched piece of nitinol, such as the stents sold by the C.R Bard Company and marketed under the name Memo-therm™. However, the stent can be any stent suitable for supporting the graft 20, and the selection of stent is in part dependent upon the particular application. For example, the stent can be selected to provide sufficient column strength to prevent kinking of the leg extension when treating a tortuous aorta. The stent can be collapsible into a radially contracted configuration suitable for delivery through an transluminal delivery system. Optionally, the stent can be self expanding and, therefore, when delivered to the treatment site within the patient's vascular system, the stent will expand from its radially contracted configuration into an expanded configuration that will fit inside the interior of the body lumen of the patient and carry blood across the diseased portion of the aorta. Additionally, the lower end of the stent may be provided with a securing mechanism, such as detents, hooks, or a flared distal end of the leg extension, by which it can engage the tissue wall of the body lumen, such as the iliac arteries, to grip against the interior tissue wall of the patient's body lumen.

As further illustrated by FIG. 3, the leg extensions 30 and 32 can include proximal end portions dimensioned for fitting within the channels 16a and 16b. The dimensions are such that the leg extension firmly engages the interior wall of the receiving channel. The firm engagement forms a fluid seal that prevents the blood or other fluid from leaking out of the implant 10. To this end, the leg extensions can be disposed within the channels sufficiently far, such as 1 cm., that in the expanded condition the outer surface of each leg extension engages the interior surface of its respective channel with sufficient frictional resistance to prevent the downward movement of the leg extensions in response to the pressure of the circulating blood. Alternatively, the stent of the leg extension can have a flared proximal end portion that, on expansion within the interior of a channel, can seal tightly against the interior wall of the channel. To further the engagement, the interior wall of the channel can have a conical and complimentary shape that dove-tails with the flared proximal end portion of the leg extensions. Optionally, the leg extensions can also include detents at their end portions 34 and 38 that can engage the interior wall of the channel to reduce mobility of the leg extension and to seal more tightly within the channel. Other techniques for engaging the leg extension to the channel, including clips, stitches, or adhesives, can be practiced with the invention without departing from the scope thereof.

Figure 4:
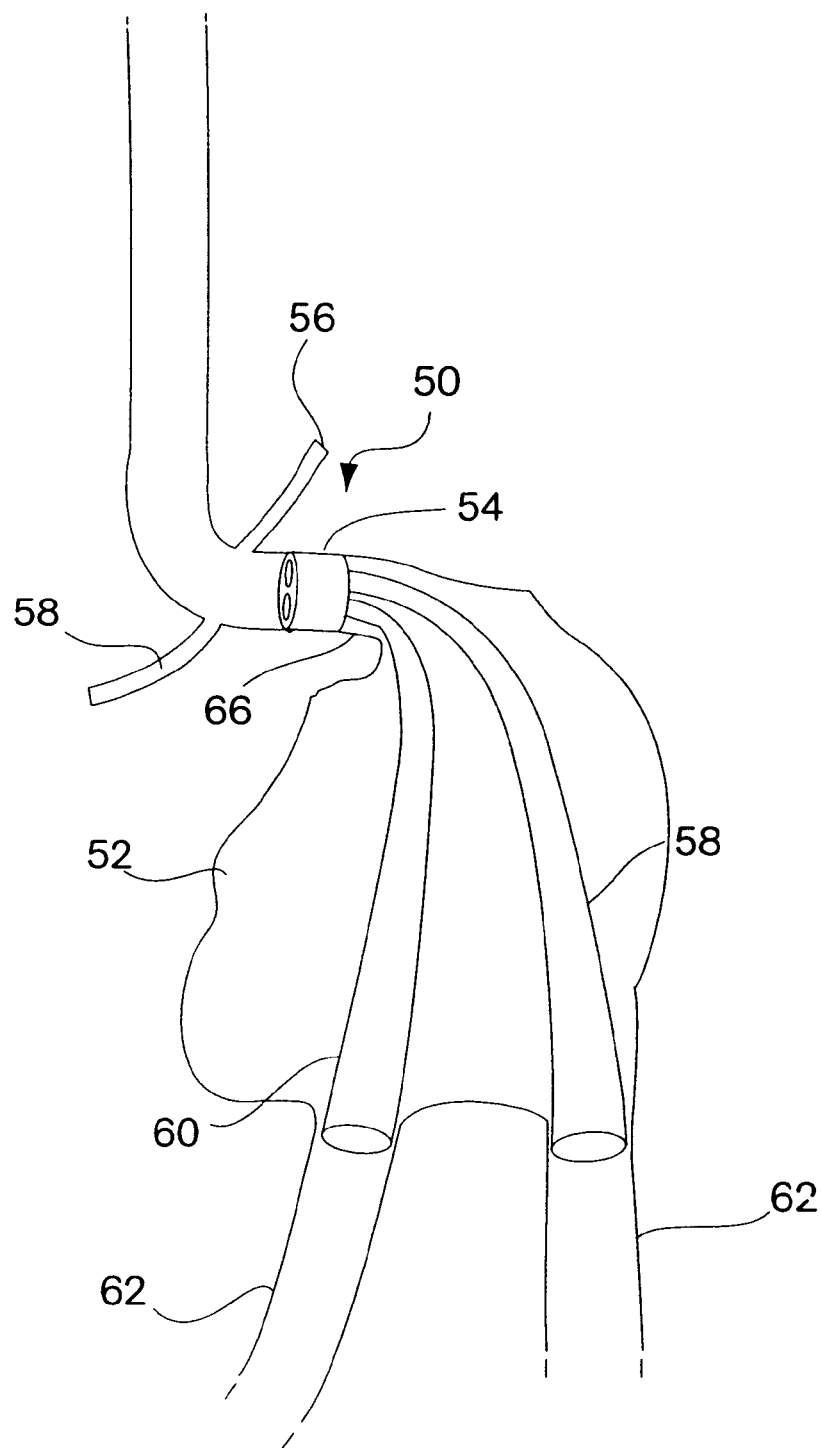
FIG. 4 depicts a short body implant having a trunk and two leg extensions and disposed within a patient's aorta.

FIG. 4 depicts the implant of FIG. 3 disposed within a torturous aorta having an abdominal aortic aneurysm 52 within the infra proximal area of the aorta. The aneurysm 52 has extended at least partially into each of the iliac arteries and has expanded the aorta in length, as well as width, causing the aorta to be tortuously formed within the patient's abdominal cavity.

The implant 50 includes a short trunk 54 and two tubular leg extensions 58 and 60. As shown in FIG. 4, the short trunk 54 is disposed generally above the area of the aneurysm 52 and below the renal arteries 56. Here at this point of the aorta, there is a short relatively straight portion of healthy tissue for receiving and engaging the trunk 54. In the depicted application, the trunk 54 of the implant 50 fits in about a 2 cm. length of healthy tissue right below the renal arteries 56. In the depicted embodiment, the trunk 54 does not extend into the aneurysm, so that the fill body of the trunk 54 is seated within and supported by the healthy portion of the aorta. Additionally, the depicted trunk 54 has a generally symmetric shape, and the circumferential portion of the trunk 54 can be fit against and be supported by the generally symmetric interior tissue wall of the aorta. The distal face 66 of the trunk 54 is proximate the renal portion of the aneurysmal sac and accessible to a surgeon who is passing a guide wire through an iliac artery and into a channel within the trunk 54. Each of the legs, 58 and 60, couple to the trunk 54 and extend into one of the respective iliac arteries 62. The distal ends of each of the legs can fit within or engage against the interior of a respective one of the iliac arteries 62, thereby providing a fluid conduit that extends from the proximal face of the trunk 54 through to the distal end of each of the tubular leg extensions 58 and 60. In this way, blood traveling downward through the aorta is redirected by the proximal face of the trunk 54 into the channels (not shown) that extend through the trunk 54 and that couple in fluid communication with the tubular leg extensions 58 and 60. Accordingly, the circulating blood bypasses the aneurysm 52 and the implant 50 prevents the fluid pressure from acting on the compromised tissue wails of the aneurysm 52, thereby reducing the risk of rupture and death.

Figure 5A:
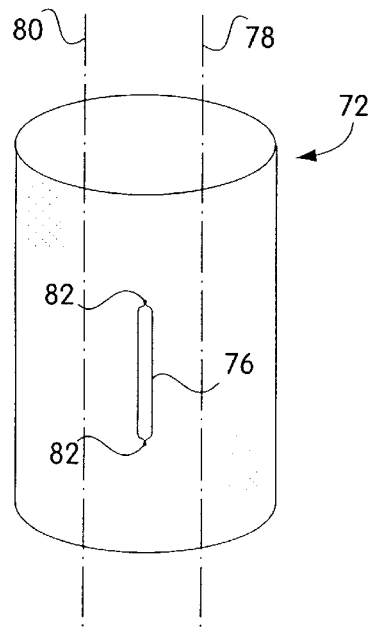
FIGS. 5a–7 depict a method for manufacturing the trunk of FIG. 1.
Figure 5C:
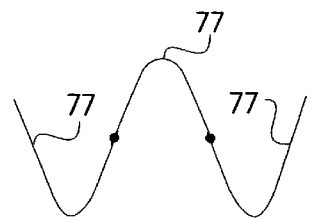
Figure 5B:
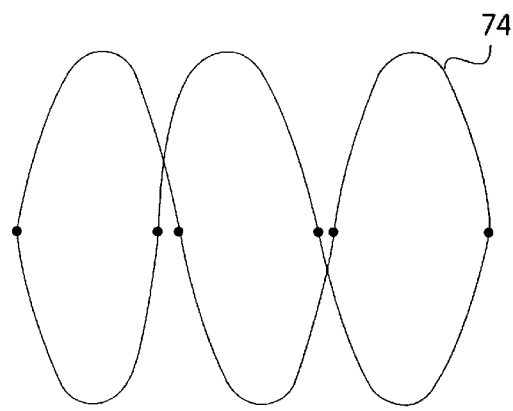

FIGS. 5a, 5b, 6 and 7 depict one method for manufacturing a trunk such as the trunk 12 depicted in FIG. 1. FIG. 5a shows a vascular graft 72 that is a tube of graft material, such as woven polyester or other bio-compatible and bio-durable material suitable for disposition within a patient's vascular system. The tube has a bifurcated section that forms two channels that extend along the axes 78 and 80. The bifurcated section is defined by a gap 76 that extends relative to the longitudinal axis of the graft 72 and that is laterally centrally disposed within the graft 72. In one practice, the stitched gap 76 is formed during a weaving process that alternates between weaving a unitary tube of fabric and weaving a bifurcated section of fabric. By weaving the bifurcated section, no seam is formed along the length of the stitched gap 76, which can eliminate or reduce any thrombosis within the graft 72 caused by blood clotting against the rough edge of a seam. In this practice, the beginning and ending points of the stitched gap 76, where the weaving process transitions between weaving a unitary body and a bifurcated section, may need to be sewn closed, as illustrated by the crotch sews 82. In an alternate practice, the graft 72 can be formed by taking a unitary tubular graft and, instead of weaving the bifurcated section, stitching a centrally and longitudinally disposed seam within the unitary body of the graft, for forming the two channels for carrying blood. Other practices for forming the bifurcated graft can be practice without departing from the scope of the invention.

Figure 6:
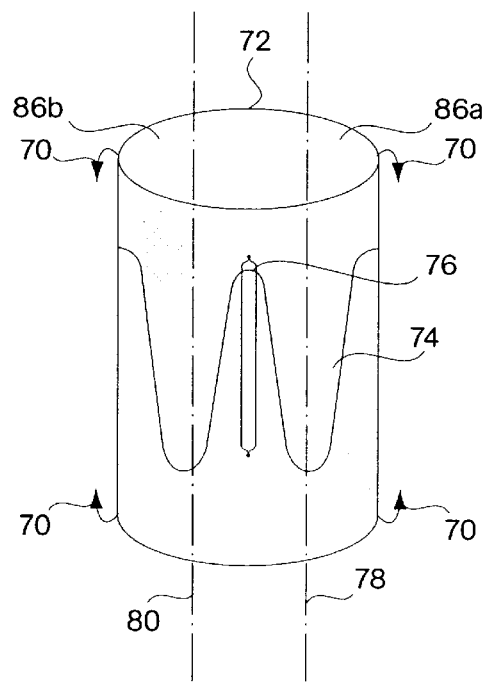

FIG. 5b depicts an anchor 74 that defines a wire frame for supporting the graft 72. The depicted anchor 74 is shaped like a hoop so that the graft 72 can be inserted within the center of anchor 74, as shown in FIG. 6. The depicted anchor 74 is formed from a plurality of oblique elements 77, each of which, as illustrated in FIG. 5c, is formed of a single wire with a rounded vertex and arms of equal length and each of which is joined at its ends to two other elements. This provides a chain of elements 77 that can be formed into a hoop by joining the two ends of the chain together.

FIG. 6 depicts a partially formed trunk 70 having a bifurcated vascular graft 72, that is centrally disposed within the anchor 74 to provide the two channels 86a and 86b that extend respectively along the axes 78 and 80. The anchor 74 is centrally disposed about the graft 72, and can optionally be attached to the g element 72 by a bio-compatible adhesive element, such as a silicone rubber adhesive, or can be joined by stitching the graft 72 to the frame of the anchor 74. As further depicted by FIG. 6, in a subsequent step, the two ends of the graft 72 are folded over the centrally disposed anchor 74, as shown by the arrows 70 of FIG. 6. Folding the ends of the graft 72 over the rims of the anchor 74 forms the proximal and distal faces of the trunk.

Figure 7:
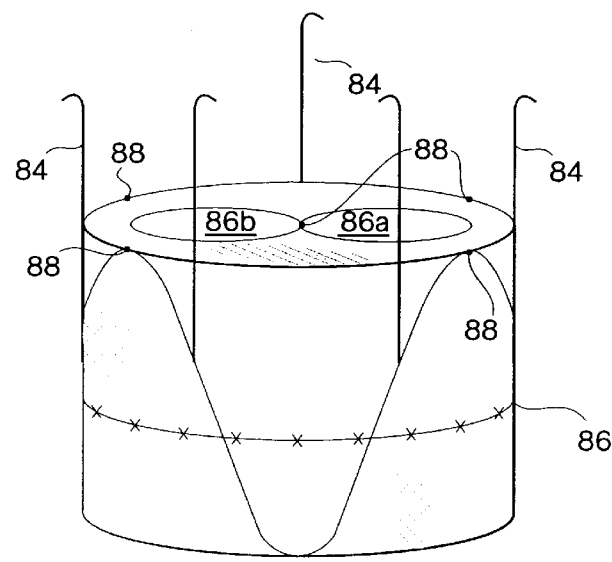

As shown in FIG. 7, after folding into the ends of the vascular graft over the centrally disposed anchor 74, the ends are joined by the stitch 76, sealing the anchor 74 within the graft 72. The stitch 76 depicted in FIG. 7 is a sutured cross stitch of the type commonly employed for joining a vascular graft to body tissue or for joining two pieces of vascular graft material. In the depicted embodiment, stitches 88 are formed within the graft 72 to secure the graft 72 to the anchor 74. Additionally, the stitches 88 are formed at the proximal openings of the channels 86a and 86b to maintain the channels open to receive the flow of blood. Stitches 88 (not shown) can be placed at the distal openings of the channels 86a and 86b to maintain the channels open to receive leg extensions. FIG. 7 further depicts that a set of hooks 84 can be attached to the anchor 74 to provide a securing mechanism that connects the implant to the interior tissue wall of the body lumen.

Figure 8:
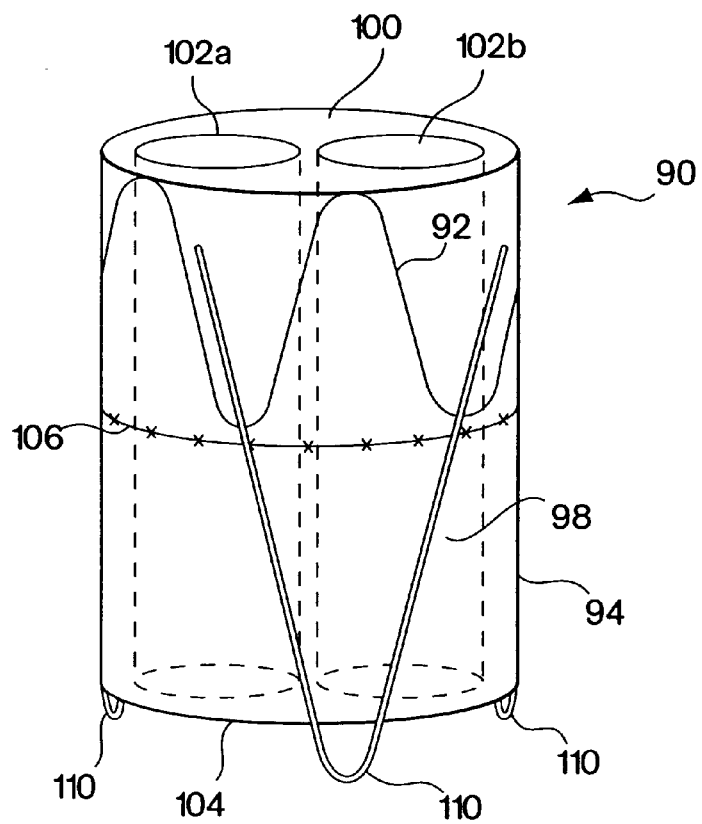
FIG. 8 depicts an alternative embodiment of a short body implant according to the invention.
Figure 9:
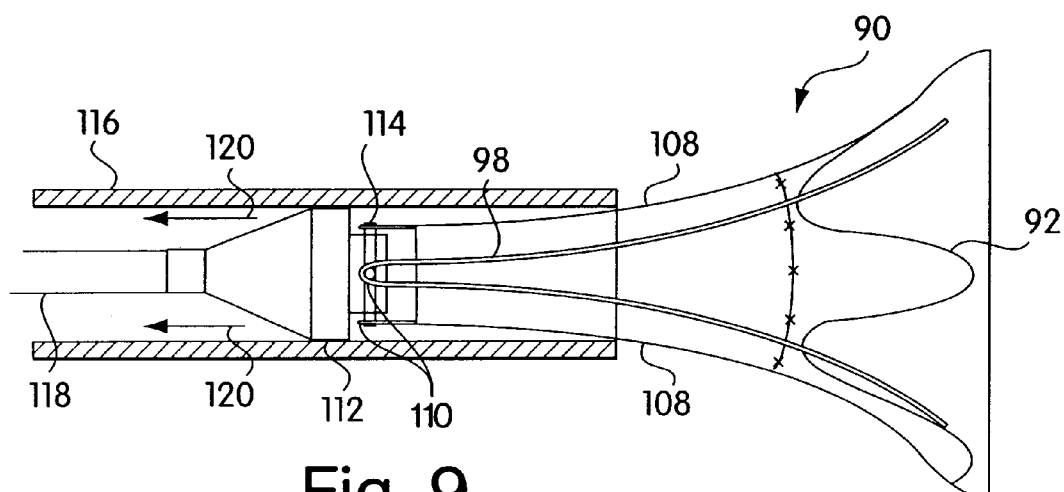
FIG. 9 depicts the short body implant of FIG. 8 partially deployed from a delivery system.

FIGS. 8 and 9 depict an alternative embodiment of the invention that includes extension loops 98 that allow for repositioning the implant 90 within the patient and that give the implant 90 an extended main body that provides a longer seating area for the leg extensions. In the depicted embodiment the implant 90 is about 4–6 cm. in length.

More particularly, FIG. 8 depicts an implant 90, having an anchor 92, a graft 94, extension loops 98, a proximal face 100, channels 102a and 102b, and a distal face 104. The graft 94 and the anchor 92 can be similar to the those anchors and grafts discussed with reference to FIGS. 1–7. In particular, the graft 94 can be formed of any of the graft materials described above with reference to FIGS. 1–7. Similarly, the anchor 92 can be formed of a flexible, resilient wire such as the anchor 74 depicted in FIG. 5b. In the depicted embodiment, the anchor 92 is approximately 1.5–3.0 cm in length and therefore extends for about half the length of the implant 90.

The extension loops 98 can also be formed from a flexible, resilient wire material. The depicted extension loops 98 are obliquely shaped resilient wire elements that are attached to the exterior surface of the graft 94. The attachment can be made by use of any suitable adhesive, by stitching the extension loop 98 to the graft 94, or by any other suitable method. As further shown in FIG. 8, each of the depicted extension loops 98 is attached to the implant 90 so that a portion of the extension loop 98 sits over the distal end of the anchor 92. A force directed radially inwardly on the extension loops 98 will cause the extension loops 98 to contract radially and push down on the flexible anchor element 94. This in turn can cause the anchor 94 to contract radially. In this contracted state, the anchor 92 will exert an outwardly directed expansion force, capable of returning the anchor 92 to its expanded configuration. Therefore, upon removal of any radially inwardly directed force, the anchor 92 will expand, and fit the exterior of the proximal end of the implant 90 against the interior tissue wall of the body lumen.

FIG. 8 further depicts that the extension loops 98 have a lower distal portion 110 that extends past the distal face 104 of the implant 90. This allows, as shown in FIG. 9, each of the distal portions 110 to form a loop that can be fit over the spokes 114 of a stay 112 of a catheter delivery device 116. One such catheter delivery system is shown and described in U.S. Ser. No. 147,498. As further shown in FIG. 9, the spokes 114 can hook one or more of the distal ends 110 of the extension loops 98. Accordingly, upon retraction of the push wire 118 in the direction of the arrows 120, the stay 112 holds the implant 90 and drags the implant 90 into the lumen of the delivery system 116. The interior wall of the lumen of the delivery device 116 butts against the extension loops 98 creating an inwardly directed radial force that causes the extension loops 98 to contract radially to fit within the lumen. As the extension loops 98 contract, they press down on the anchor 92, to partially collapse the anchor 92, thereby allowing the anchor 92 to be retracted into the lumen of the delivery system 116. This allows a doctor to recapture and reposition an implant 90 that has been partially deployed within the patient's vascular system.

Figure 10:
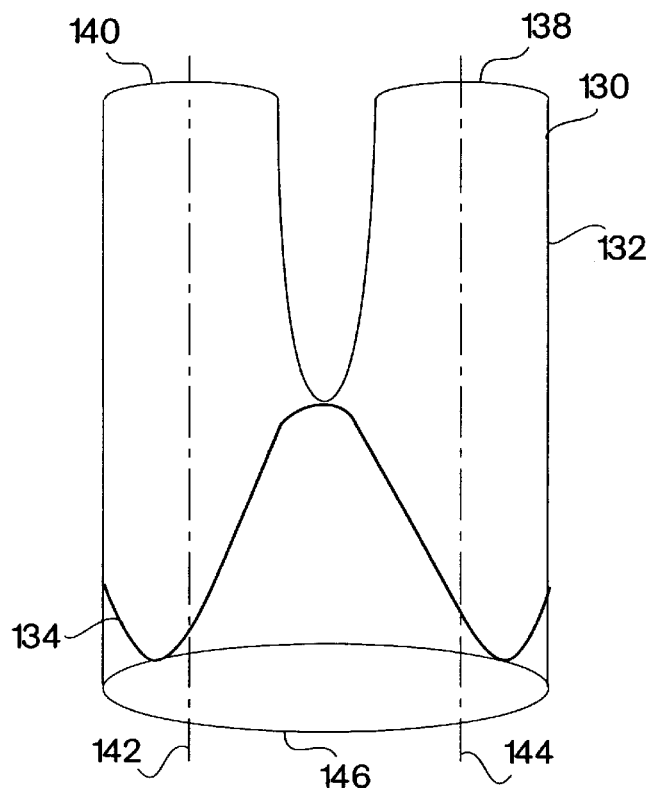
FIGS. 10–11 depicts a further alternative embodiment of the invention having an anchor located adjacent a proximal end of the trunk.
Figure 11:
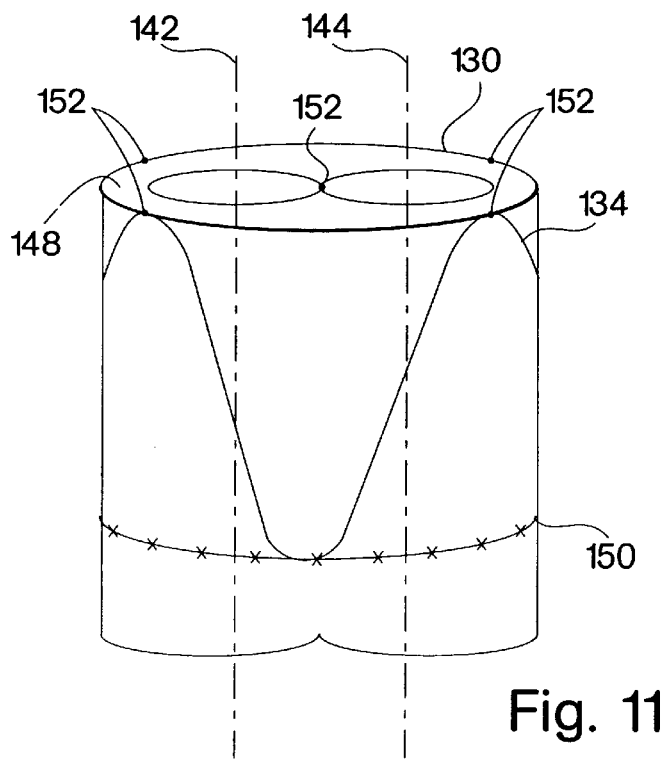

FIGS. 10 and 11 depict a further embodiment of the invention. In this embodiment, the short body implant is formed from a U-shaped bifurcated graft 132, which can be made of woven polyester, PTFE or any other suitable material. As shown in FIG. 10, the proximal end 146 of the graft 132 is formed as a cylindrical port. The opposite end of the graft 132 is formed as a pair of bifurcated legs, 138 and 140, each of which is formed as a lumen longitudinally extending along one of the respective axes 142 or 144. Each of the legs 140 and 138 have a length approximately equal to the length of the anchor 134. As will be shown with reference to FIG. 11, this allows each of the legs 140 and 138 to be pushed into and passed through the proximal port 146. FIG. 10 further depicts that an anchor 134 is disposed at the proximal end 146 of the implant 130 and inside the graft 132. The anchor 134 can be similar to the anchors described with reference to FIGS. 1–7.

In FIG. 11, the implant 130 is shown wherein the legs 140 and 138 have been passed through the proximal end 146 to form the proximal face 148 of the implant 130. In the embodiment depicted in FIG. 11, the anchor 134 is enclosed within the material of the graft 132. A stitch 150 joins the graft material to enclose the anchor 134 and optional stitches 152 can be placed on the proximal face to maintain the ports of the channels extending along axes 142 and 144 in an open condition.

Figure 12:
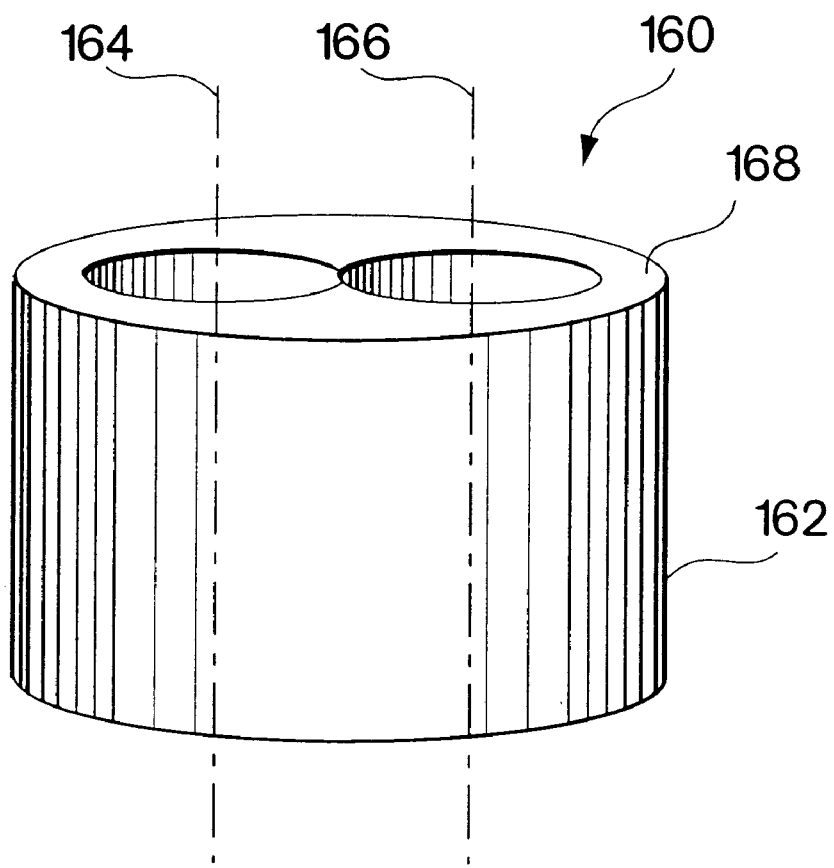
FIG. 12 depicts further alternative embodiment of the invention having a solid trunk body.

FIG. 12 depicts a further alternative embodiment of the short body implant according to the invention. FIG. 12 depicts a trunk 160 of an implant. The trunk 160 includes a plug of bio-compatible and bio-durable material, such as ePTFE, in which two longitudinally extending bores 164 and 166 are provided. Each of the bores 164 and 166 extends completely through the body of the implant 164 to provide for a bifurcated flow of blood. To this end, the trunk 160 has a proximal face 168 formed by one surface of the solid plug.

The proximal face 168 redirects blood into the two bores 164 and 168 to provide a bifurcated flow of blood. In one embodiment, the trunk 160 is formed of a compressible material such as ePTFE, so that the trunk 160 can be radially compressed for fitting within the lumen of a transluminal delivery system. Upon delivery, the compressed implant will expand so that the outer periphery 162 of the trunk 160 will seal against the interior issue wall of the vessel. In the expanded condition, the bores 164 and 166 can receive leg extensions, such as the leg extensions described with reference to FIGS. 1–7.

Figure 13:
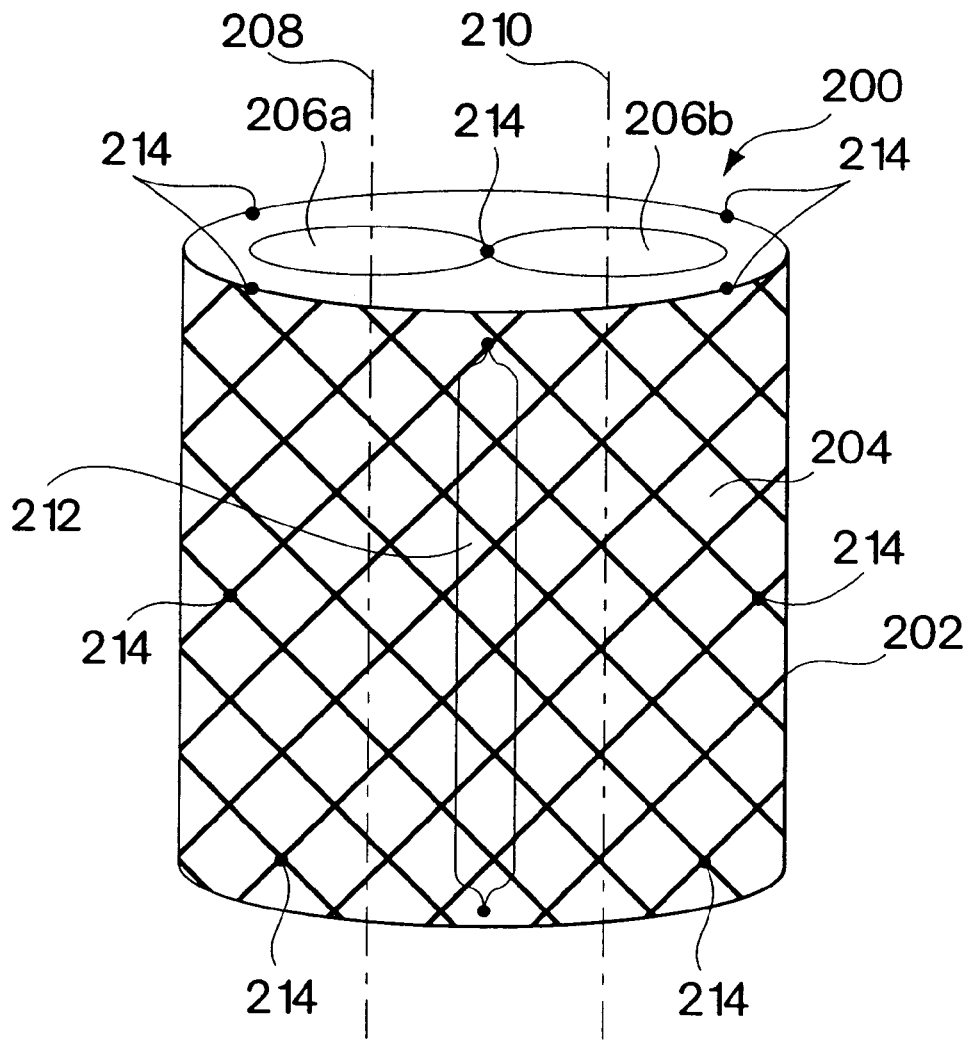
FIG. 13 depicts further alternative embodiment of the invention.

FIG. 13 depicts another alternative embodiment of the invention. In particular, FIG. 13 depicts a trunk 200 for an implant according to the invention, wherein the trunk 200 includes a stent 202, a bifurcated graft 204, two channels 206a and 206b, that extend along the longitudinal axes 208 and 210 respectively, a gap 212 that extends longitudinally within the graft 204, and stitches 214 that attach the graft to the stent and hold the ports of the channels 206a and 206b open for receiving blood at the proximal face and for receiving leg extensions at the distal face.

The depicted stent 202 can be a Palmaz-type stent similar to the stents of leg extensions 30 and 32 described above with reference to FIG. 3. The wire frame of the stent 202 supports the graft 204 and also acts as an anchor element that can seal against the interior tissue wall of the aorta. The stent 202 is radially contractible for fitting within a lumen of a catheter delivery system. In one embodiment the stent 202 is formed of nitinol and upon activation by for example the patient's body heat, will expand into the open configuration shown in FIG. 13. Optionally, hooks, detents, or other securing mechanisms can be attached to the stent 202 for reducing or eliminating downstream movement of the trunk 200 caused by the force of blood circulating through the aorta.

The graft 204 can be similar to the graft depicted in FIG. 5a which includes a bifurcated mid-section. In the embodiment depicted in FIG. 13, the graft 204 is fitted within the stent 202 and attached by stitches 214 to the stent 202. In the depicted embodiment, the bifurcated section of the graft 204 extends for almost the full length of the stent 202. This is illustrated by showing the gap 212, that defines the bifurcated section, as extending almost completely through the stent 204. To place the bifurcated section in the stent 202, a graft 204, such as the graft depicted in FIG. 5a, is disposed within the center of the stent 202 and both ends of the graft are cut to be substantially flush with the proximal and distal ends of the stent 202. The ends of the graft are then stitched, glued or otherwise bonded to the rims of the stent 202. Alternatively, as described with reference to FIGS. 5–7, the ends of the graft 204 could have been folded over the sides of the stent 202 to bring the ends of the bifurcated section flush with the ends of the stent 202. In either case, the proximal and distal ends of the graft 202 are secured to the rims of the stent 202 so that when the stent 202 expands from a contracted to an expanded configuration, the rims pull the graft 204 to form proximal and distal faces for the trunk 200. The trunk 200 and the channels extending therethrough can be dimensionally adapted to receive leg extensions, such as the leg extensions 30 and 32 described above.

Figure 14A:
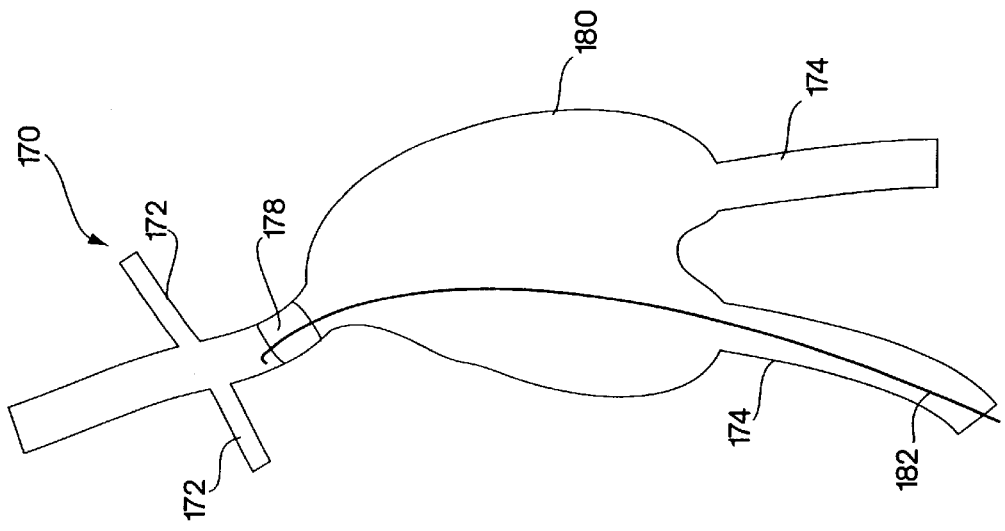

FIGS. 14a–d depict one process for forming a bifurcated implant within the aorta and iliac arteries of a patient. In particular, FIG. 14a depicts an aorta 170, renal arteries 172, iliac arteries 174, a leg extension 176 and an aneurysm 180 that extends at least partially into the proximal ends of the iliac arteries 174. FIG. 14a further depicts that the trunk 178 of an implant according to the invention is disposed, typically by transluminal delivery, within a short healthy renal neck of the aorta 170. Similarly, the leg extension 176 can be delivered transluminally and can be delivered over the same guidewire employed to deploy the trunk 178. The delivery procedure for the leg extension 176 and the leg extension 184, depicted in FIG. 14c are similar and will be understood from the description of the delivery of the leg extension 184 described below.

Figure 14B:
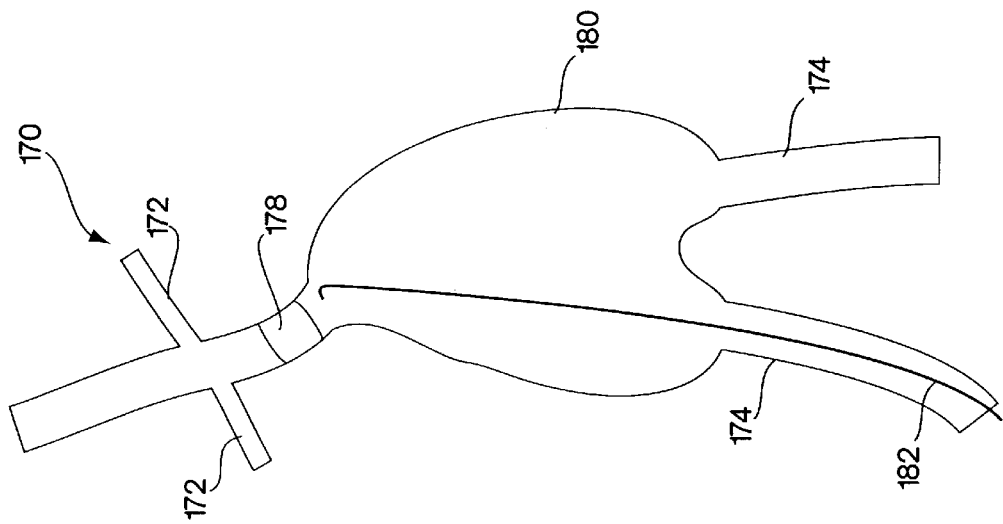

As shown in FIG. 14a, a guidewire 182 is fed through one of the iliac arteries 174 and into the aneurysmal sac. In a subsequent step, as shown in FIG. 14b, the guidewire 182 can be guided by the surgeon through one of the channels that extends through the trunk 178. Once the guidewire 182 is passed through the channel of the trunk 178, a delivery catheter 184, shown in FIG. 14c, can be fed over the guidewire and into one channel of the trunk 178. The delivery device can be loaded with one of the leg extensions, such as the leg extensions 30 or 32. The delivery device then is advanced over the initially placed guidewire 182 until its leading upper end is disposed as desired within the trunk 178. As shown in FIG. 14d, the leg extension may be advanced into one of the channels extending through the trunk 178 to dispose the proximal end of the inserted leg extension beyond the distal face of the implant 178 and into the channel. As described above, the outer surface of the depicted leg extension 188 can functionally engage against the inner surface of the channel extending through implant 178 to secure and seal the leg extension 188 at the channel of the trunk 178. When the leg extension 188 is so placed the delivery device 184 is withdrawn to enable the leg extension 188 to expand. The length and diameter of the leg extension 188 is selected so that the upper end will securely engage within the trunk, and so that the leg extension 188 will span the aneurysm 180, and that at least a portion of the leg extension 188 will be seated within the common iliac artery 174. When the delivery device has been withdrawn, the trunk 178 and leg extension 188 will remain within the patient. In this way, a bifurcated endovascular graft can be formed within the vascular system of the patient.

It will be understood that the embodiments of the invention which have been described are illustrative of some of the applications and principles of the present invention. Various modifications may be made by those skilled in the art without departing from the spirit and scope of the invention. For example, different materials and shapes can be employed for forming the different elements of the implants, such as employing plastics for forming the anchors, and the extension loops. Moreover, it will be understood that the systems of the invention can be applied during conventional surgical techniques that employ open surgery, and that in these applications, the implants need not be radially compressible for fitting in a lumen of a delivery device. Additionally, the implant can comprise a bifurcated stent and vascular graft that wraps around the body of the bifurcated stent or, optionally, fits inside the body of the bifurcated stent. The bifurcated stent can be radially compressible and expandable to allow for transluminal delivery. Other modifications, substitutions and additions can be made without departing from the scope of the invention. Accordingly, the invention is not to limited to the above shown illustrated embodiments, but is to be understood by the claims set forth below, which are to be interpreted as broadly as allowed by law.

I claim:

1. An endoprosthetic implant, comprising a trunk having, a proximal face including an aperture disposed therein, a channel in fluid communication with said aperture and extending from said proximal face and hang a portion adapted for coupling to a leg extension, an anchor coupled to a peripheral portion of said proximal face and adapted for engaging said proximal face to an interior tissue wall of a body lumen wherein said anchor comprises a tubular wire frame having a proximal opening and a distal opening, and a vascular graft having a bifurcated portion disposed within said tubular wire frame and having a first and second channel and a peripheral portion mounted to said proximal opening of said tubular wire frame for forming said proximal face.

2. An endoprosthetic implant according to claim 1, wherein said proximal face comprises a substantially flat surface formed of a fluid resistant, bio-compatible material suitable for disposition within a flow of fluid that occurs within the body lumen, said proximal face being adapted to redirect fluid flow through said channel.

3. An endoprosthetic implant according to claim 1, wherein said anchor is radially compressible for allowing said trunk to be carried within a lumen of a catheter delivery system.

4. An endoprosthetic implant according to claim 1, wherein said anchor includes a resilient wire frame capable of being placed under compression for providing a radially expansive force for sealing said trunk against the tissue wall of the body lumen.

5. An endoprosthetic implant according to claim 1, wherein said trunk is dimensionally adapted for disposition within a short section of the body lumen, for disposition above a site of an aneurysm.

6. An endoprosthetic implant according to claim 1, wherein said trunk has a longitudinal length between approximately 1.0 cm.–3.0 cm.

7. An endoprosthetic implant according to claim 1, further comprising a tubular leg extension having an interior channel and having an upper end being contractible radially for insertion into said channel and being dimensionally adapted for spanning an aneurysm.

8. An endoprosthetic implant according to claim 1, farther comprising hook elements coupled to said trunk for joining said trunk to the tissue of the body lumen.

9. An endoprosthetic implant according to claim 1, wherein said anchor is disposed proximate said proximal face.

10. An endoprosthetic implant according to claim 9, further including an extension loop frame having a distal loop portion for coupling to a spoke element of a catheter delivery system, whereby said catheter delivery system may deliver, recapture and reposition said implant within the body lumen.

11. An endoprosthetic implant, comprising a trunk having, a proximal face including an aperture disposed therein, a channel in fluid communication with said aperture and extending from said proximal face and having a portion adapted for coupling to a leg extension, and an anchor coupled to a peripheral portion of said proximal face and adapted for engaging said proximal face to an interior tissue wall of a body lumen, wherein said trunk comprises a solid plug of biocompatible material having two interior passageways extending therethrough for defining a first and second channel.

12. An endoprosthetic implant according to claim 11, wherein said biocompatible material is elastomeric.

13. A method of forming a bifurcated implant, comprising the steps of providing an anchor formed of a resilient wire frame capable of big radially compressed and having a generally tubular shape including a proximal opening and a distal opening, providing a vascular graft having a bifurcated portion and a proximal portion coupled thereto, wherein said step of providing a vascular graft includes the step of providing a bifurcated graft having a proximal portion formed as a unitary channel and having a bifurcated portion formed as two legs extending from said unitary channel, disposing said bifurcated portion within said anchor, and mounting said proximal portion of said graft to said proximal opening of said anchor to form a face for said implant having at least one opening for receiving fluid.

14. A method of forming a bifurcated implant, comprising the steps of providing an anchor formed of a resilient wire frame capable of being radially compressed and having a generally tubular shape including a proximal opening and a distal opening, providing a vascular graft having a bifurcated portion and a proximal portion coupled thereto, wherein said stop of providing a vascular graft includes the step of providing a bifurcated graft woven from a biocompatible material and having a bifurcated section formed therein, disposing said bifurcated portion within said anchor, and mounting said proximal portion of said graft to said proximal opening of said anchor to form a face for said implant baying atleast one opening for receiving fluid.

15. A method of forming a bifurcated implant, comprising the steps of providing an anchor formed of a resilient wire frame capable of being radially compressed and having a generally tabular shape including a proximal opening and a distal opening, providing a vascular graft having a bifurcated portion and a proximal portion coupled thereto, wherein said step of providing a vascular graft includes the step of providing a graft formed as a unitary tubular body, placing a stitch within said unitary tubular body along a centrally located longitudinal axis to form said bifurcated portion, disposing said bifurcated portion within said anchor, and mounting said proximal portion of said graft to said proximal opening of said anchor to form a face for said implant having at least one opening for receiving fluid.

* * * * *

UNITED STATES PATENT AND TRADEMARK OFFICE
CERTIFICATE OF CORRECTION

PATENT NO. : 6,306,164 B1
DATED : October 23, 2001
INVENTOR(S) : Dennis Kujawski It is certified that error appears in the above-identified patent and that said Letters Patent is hereby corrected as shown below:

<u>Title page,</u>
Item [75], should read -- [75] Inventor(s):
Dennis Kujawski, Brookline, NH (US)
Michael F. Weiser, Groton, MA (US) --

Signed and Sealed this

Twenty-eighth Day of January, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,306,164 B1
DATED         : October 23, 2001
INVENTOR(S)   : Dennis Kujawski and Michael F. Weiser It is certified that error appears in the above-identified patent and that said Letters Patent is hereby corrected as shown below:

Column 4,
Line 12, replace "contractile" with -- contractible --.
Lines 42-43, replace "selfpanding" with -- self-expanding --.

Column 6,
Line 32, replace "sewn" with -- seam --.
Line 61, replace "ofthe" with -- of the --.

Column 7,
Line 35, replace "ace" with -- face --.

Column 10,
Line 17, replace "fill" with -- full --.
Line 38, replace "wails" with -- walls --.

Column 11,
Line 16, replace "g element" with -- graft element --.

Column 12,
Line 45, replace "port" with -- end --.

Column 13,
Line 8, replace "issue" with -- tissue --.

Column 14,
Line 26, replace "functionally" with -- frictionally --.
Line 28, replace "at the" with -- against the --.

Column 15,
Line 2, replace "hang" with -- having --.
Line 47, replace "farther" with -- further --.

UNITED STATES PATENT AND TRADEMARK OFFICE
CERTIFICATE OF CORRECTION

PATENT NO.     : 6,306,164 B1
DATED          : October 23, 2001
INVENTOR(S)    : Dennis Kujawski and Michael F. Weiser It is certified that error appears in the above-identified patent and that said Letters Patent is hereby corrected as shown below:

Column 16,
Line 14, replace "big" with -- being --.
Line 37, replace "stop" with -- step --.
Line 46, replace "baying atleast" with -- having at least --.
Line 52, replace "tabular" with -- tubular --.

Signed and Sealed this

Eleventh Day of May, 2004

JON W. DUDAS
*Acting Director of the United States Patent and Trademark Office*

EX PARTE REEXAMINATION CERTIFICATE (5508th)
United States Patent
Kujawski et al.

(10) Number: US 6,306,164 C1
(45) Certificate Issued: Sep. 12, 2006

(54) SHORT BODY ENDOPROSTHESIS

(75) Inventors: Dennis Kujawski, Brookline, NH (US); Michael F. Weiser, Groton, MA (US)

(73) Assignee: C.R. Bard, Inc., Murray Hill, NJ (US)

Reexamination Request:
No. 90/007,173, Aug. 13, 2004

Reexamination Certificate for:
Patent No.: 6,306,164
Issued: Oct. 23, 2001
Appl. No.: 08/925,809
Filed: Sep. 5, 1997

Certificate of Correction issued Jan. 28, 2003.

Certificate of Correction issued May 11, 2004.

(51) Int. Cl.
*A61F 2/00* (2006.01)

(52) U.S. Cl. ............... 623/1.35; 623/1.36; 623/1.16
(58) Field of Classification Search ............ 623/1.35
See application file for complete search history.

(56) References Cited

U.S. PATENT DOCUMENTS

| | | | |
|---|---|---|---|
| 5,733,325 A | 3/1998 | Robinson et al. | 623/1 |
| 6,325,819 B1 | 12/2001 | Pavcnik et al. | 623/1.11 |

FOREIGN PATENT DOCUMENTS

| | | |
|---|---|---|
| DE | 93 19 267.3 | 4/1994 |
| WO | WO 95/16406 | 6/1995 |
| WO | WO 98/07389 | 2/1998 |

OTHER PUBLICATIONS

International Search Report, PCT application PCT/US 98/18662.

International Preliminary Examination Report, PCT application PCT/US 98/18662.

Claims filed in PCT application PCT/US 98/18662.

*Primary Examiner*—David O. Reip

(57) ABSTRACT

The invention comprises, inter-alia, endoprosthetic implants for treating vascular defects, including abdominal aortic aneurysms. Implants according to the invention have a short main body that can be positioned within a patient's aorta at a position above the renal end of an aortic aneurysm. The short main body includes a proximal, or renal, face that redirects the flow of blood into the openings of channels that can carry blood past the aneurysm. In this way, the flow of blood through the aorta is diverted into the two passageways and through the main body of the implant. Fluid exiting the implant can be carried by leg extensions and delivered to a healthy part of the patient's aorta or the iliac arteries. Accordingly, the implant provides a system for allowing blood traveling through the aorta to be carried by a vascular graft that spans an aortic aneurysm, thereby relieving fluid pressure on the thin wall of aortic aneurysm, and reducing the risk of death caused by a ruptured aneurysm.

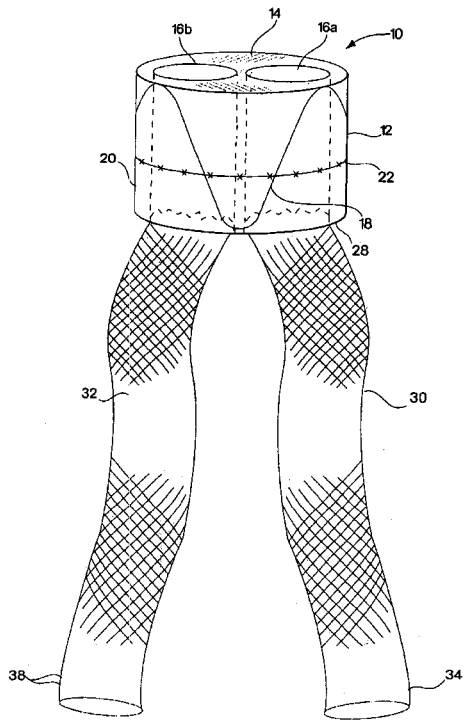
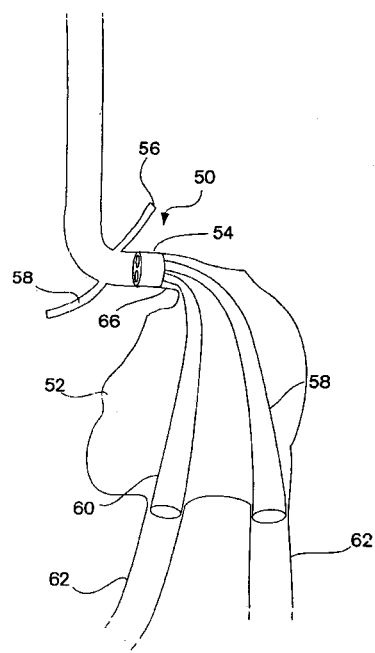

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

* * * * *